United States Patent [19]

Sonneborn et al.

[11] Patent Number: 4,751,183

[45] Date of Patent: Jun. 14, 1988

[54] MONOCLONAL ANTIBODY THAT RECOGNIZES A STRUCTURE COMMON TO HUMAN INTERLEUKIN-2 (TCGF) AND TO THE LIGHT LAMBDA CHAIN OF HUMAN IMMUNOGLOBULIN AND LINES OF HYBRIDOMA CELLS THAT PRODUCE THESE MONOCLONAL ANTIBODIES

[75] Inventors: Hans H. Sonneborn, Heusenstamm; Rolf M. Vornhagen, Langen; Udo Schwulera, Bad Vilbel, all of Fed. Rep. of Germany

[73] Assignee: Biotest-Serum-Institut GmbH, Frankfurt, Fed. Rep. of Germany

[21] Appl. No.: 641,084

[22] Filed: Aug. 15, 1984

[30] Foreign Application Priority Data

Aug. 16, 1983 [DE] Fed. Rep. of Germany ....... 3329449

[51] Int. Cl.$^4$ ........................... C12N 5/00; C12R 1/91; C07K 15/04; A61K 39/395
[52] U.S. Cl. .................................. 435/240.27; 435/68; 435/948; 935/104; 935/110; 436/548; 530/351
[58] Field of Search ...................... 435/68, 172.2, 240, 435/241, 948, 240.27; 436/548; 935/104, 110; 530/351

[56] References Cited

U.S. PATENT DOCUMENTS 4,473,493  9/1984  Gillis et al. ........................... 435/241

OTHER PUBLICATIONS

Stadler et al, "Monoclonal Antibody Against Human Interleukin 2 (IL-2) Journal of Immunology 128(4) pp. 1620-1624 (1982).

Stadler et al, "Human Interleukin-2: Biological Studies Using Purified IL-2 and Monoclonal Antibodies", Lymphokines vol. 6 pp. 117-135 (1982).

Smith et al, "Production and Characterization of Monoclonal Antibodies to Human Interleukin 2" Journal of Immunology 131(4) pp. 1808-1815 (1983).

Gillis et al, "The Biochemical and Biological Characterization of Lymphocyte Regulatory Molecules", Journal of Immunology 126(5) pp. 1978-1984 (1981).

Francis W. Ruscetti, James W. Mier, and Robert C. Gallo-Human T-Cell Growth Factor: Parameters for Production-Journal of Supramolecular Structure 13:229-241 (1980).

G. Köhler et al, "Continuous Cultures of Fused Cells Secreting Antibody of Predefined Specificity"; Nature vol. 256, (1975) pp. 495-497.

Kearney et al, "A New Mouse Myeloma Cell Line that has Lost Immunoglobulin Expression . . . ", J. of Immun., vol. 23, No. 4, Oct. 19.

P. Lindsay et al, "The Species Specificity of Human Interleukin 2", Human Lymphokines, Academic Press (1982); pp. 479-485.

Sonneborn and Schwulera, "Production, Purification & Properties of Human Interleukin-2 (IL-2)", Technical Reports, *Biotest Bulletin* 3: (1982), pp. 222-227.

Köhler & Milstein, "Derivation of Specified Antibody-Producing Tissue Culture . . . ", *Eur. J. Immunol.* (1976) 6:511-519.

Cotton et al, "Somatic mutation and the origin of antibody diversity . . . Eur. J. Immunol. (1973), 3:135-140.

Morgan et al, "Selective In Vitro Growth of T-Lymphocytes from Normal Human Bone Marrows", Science vol. 193. (1976), 3:1007-1008.

*Primary Examiner*—John E. Tarcza
*Attorney, Agent, or Firm*—Sprung Horn Kramer & Woods

[57] ABSTRACT

Monoclonal antibodies that recognize a structure common to human interleukin-2 and to the light λ chain of human immunoglobulin and lines of hybridoma cells that produce these monoclonal antibodies can be prepared by immunizing animals, especially mice, with human interleukin-2 (TCGF) and fusing the splenocytes obtained from the animals with animal, expecially mouse, myeloma cells to create a hybridoma. The hybridomas are raised as clones and the antibodies obtained from the individual clones tested for their specificity to human interleukin-2 (TCGF). Clones that produce antibodies with a specificity to human interleukin-2 (TCGF) are selected for further raising to prepare the antibody. The antibody is harvested from the culture medium or from the ascitic fluids of the animal, especially the mouse, with the hybridoma.

14 Claims, 3 Drawing Sheets

MW
x10³

66-

45-

26-

18-
14-

BJ:  λ   κ

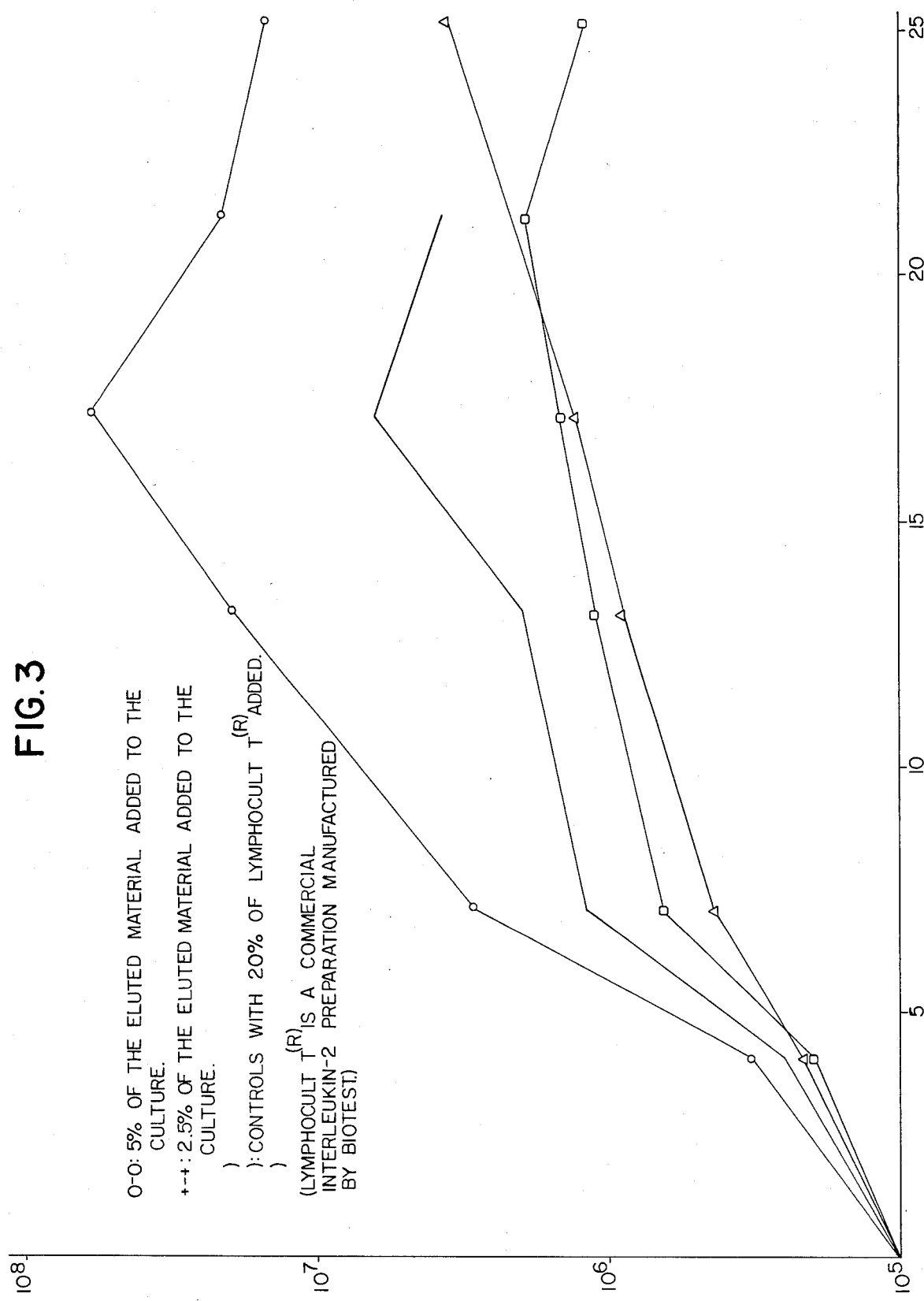

MONOCLONAL ANTIBODY THAT RECOGNIZES A STRUCTURE COMMON TO HUMAN INTERLEUKIN-2 (TCGF) AND TO THE LIGHT LAMBDA CHAIN OF HUMAN IMMUNOGLOBULIN AND LINES OF HYBRIDOMA CELLS THAT PRODUCE THESE MONOCLONAL ANTIBODIES

The invention concerns monoclonal antibodies that recognize a structure common to human interleukin-2 (TCGF) and to the light chain of human immunoglobulin and lines of hybridoma cells that produce these monoclonal antibodies.

The abbreviatons

| | |
|---|---|
| TCGF for | T-lymphocyte growth factor |
| MLC | mixed-lymphocyte culture |
| PEG | polyethylene glycol |
| PHA | phytohemagglutinin |
| SDS | sodium dodecylsulfate |
| POD | peroxidase |
| IL-2 | interleukin-2 |
| BJ | Bence Jones protein |
| HSA | human serum albumin |
| MAB | monoclonal antibody |
| Con A | concanavalin A |
| MW | molecular weight | will be employed herein in the description and claims. Interleukin-2 (IL-2, TCGF) is a lymphokine and plays a decisive part in the regulation of the immune response.

This factor, first described in 1976 by Morgan et al. [1/*Science* 193, 1007 (1976)], assumes a central position in the development of the immune response. A resting T lymphocyte is sensitized and activated for example by an antigen and accordingly obtains a signal. The same antigen, however, also stimulates macrophages and helper T lymphocytes, that release a second signal in the form of interleukin-2 to the activated T lymphocyte, subsequent to which the cell begins to proliferate.

The obtaining of raw human interleukin-2 has been described by a number of authors including F. W. Ruscetti and R. C. Gallo "Regulation of the production and release of human T cell growth factor," *J. Supramol. Biol.* 13 (1980)] and P. Lindsay, U. Schwulera, and H. H. Sonneborn "The species specificity of Interleukin-2," 3rd *International Lymphokine Congress,* Dallas, Texas, Oct. 14–17, 1981].

Various methods of purification, e.g. as described in German Offenlegungsschrift No. 3 149 360, are also known.

A combination of methods for preparing and purifying, and a recitation of properties of interleukin-2 is available from *Biotest Bulletin* 3, 222–27 (1982).

Since only expensive biological tests have been available for measuring the activity of interleukin-2 up to now, a technique for determining interleukin-2 by means of a monoclonal antibody would be of great significance both for identifying the protein and in order to have a simple and reproducible test available.

Such an antibody would also make it possible to purify the protein (for use as a therapeutic product, for example).

European Patent Application No. 0 064 401 already describes a monoclonal antibody that inhibits the activity of interleukin-2. This antibody, however, can only adsorb activity and is not capable of releasing it again. As described in that document, no activity can be eluted from the antibody columns.

Biotest Bulletin, supra, describes the preparation of hybridomas that were positive in the Elisa test and that inhibited the action of interleukin-2 in a $^3$H-thymidine-incorporation assay. No method of describing and identifying the resulting antibodies is set forth in the reference.

The object of the present invention is to provide a way of identifying and detecting interleukin-2 (IL-2, TCGF) better, in patients for example, and of purifying and characterizing it better.

This object is attained in accordance with the invention by the preparation of both a line of hybridoma cells that allows the production of an antibody that recognizes a structure common to human interleukin-2 (TCGF) and to the light λ chain of human immunoglobulin and of the antibody produced.

It has, surprisingly, been discovered that the antibody in accordance with the invention recognizes a structure that is common to human interleukin-2 (TCGF) and to the light chain of human immunoglobulin and that can accordingly be more precisely defined and that it adsorbs all of the interleukin-2 activity, a considerable portion of which can be eluted therefrom in an active form. The antibody in accordance with the invention is accordingly appropriate, once the light λ chain has been removed, for highly specific interleukin-2 purification.

An essential advance is that both cloned and non-cloned T lymphocytes and MLC, PHA, and Con A blasts of animal and human origin can be multiplied over a relatively long time with material eluted from a column of the monoclonal antibodies in accordance with the invention in comparison with an interleukin-2 preparation.

Monoclonal antibodies can be obtained by immunizing an animal with an antigen, harvesting antibody-producing cells from the animal, and fusing the antibody-producing cells with lines of tumor cells, myeloma cells for example, resulting in hybridomas that are then isolated and will produce the monoclonal antibodies Köhler, G. and Milstein, C., *Eur. J. Immunol.* 6, 511–19 and Köhler, G. and Milstein, C., *Nature* 256, 495 (1975)].

The cells of the hybridoma obtain the ability to produce a very specific antibody from one "parent" and owe their capacity to keep on dividing for a long time to the other.

These hybridoma can be raised either in vitro or as tumors in a host animal.

Since each antibody-producing cell (clone) only creates monoclonal antibodies of a single specificity, monoclonal cultures of the hybridomas raised from such a clone with one specificity will always produce a homogeneous antibody that can be obtained either from the culture medium of hybridoma cultures in vitro or from the cells, ascitic fluids, or sera of tumorous host animals.

The homogeneity and high specificity of the monoclona antibodies manufactured in this way makes them especially valuable for diagnostic purposes.

To induce production of monoclonal antibodies with specificity against human interleukin-2 (TCGF), animals are immunized with a purified preparation of interleukin-2 (TCGF). Although the particular species of animal is not critical, the strain should be genetically well defined. Mice are usually employed because various inbred strains of this animal exist that are genetically well defined and because various neoplastic cells of murine origin can also be obtained as well characterized cultures. Other species of animals can, however, also be utilized.

A suspension of splenocytes is then prepared and washed. The resulting antibody-producing cells are fused with neoplastic cells. Individual tumor cells, especially myeloma cells, can be fused in a practical way with the antibody-producing cells and yield viable antibody-producing hybridoma cultures. The tumor cells and antibody-producing cells should preferably derive from the same species since this increases the probability that the genetic and biochemical properties of the parent cells will be compatible and that they will accordingly produce viable hybridomas.

There is a number of well characterized lines of myeloma cells that can be employed in accordance with the invention. Examples are P3-X63-Ag8, P3-X63-Ag8.653, S 194, Y3, SP2/0, and MPC-11 and their derivatives. The P3-X63-Ag8.653 Kearney et al., *J Immunol.* 123, 1548 (1979)]line deposited as Number I-251 with the CNCM (French National Collection of Microorganism Cultures) on October 6, 1983 is preferably employed. Preferably employed is a myeloma line that produces no antibodies, so that the resulting hybridoma will only produce antibody chains of the parent splenocyte or lymph-node cell.

Myeloma cells and cells obtained from mice immunized with the human interleukin-2 preparation are fused by the the method of Köhler and Milstein, Eur. J. Immunol, supra.

The hybridomas are then selected, with any growth indicating successful hybridization of mouse splenocytes and mouse myeloma cells.

Hybridoma clones can be raised in vitro by the known tissue-culture methods like that described by Cotton et al. *Eur. J. Immunol.* 3, 136 (1973)]. The hybridomas can, however, also be raised if desired in vivo in the form of tumors in a histocompatible animal or in athymic hairless mice. The antibodies can be harvested from the in vitro culture medium or from the serum or ascitic fluid of the animal by known methods.

The specificity of the antibody of each clone to interleukin-2 (TCGF) is determined by known test methods, and clones that produce antibodies with the desired specificity selected.

The invention will now be described with reference to the following example and the accompanying drawings, wherein:

FIG. 3 is a graph showing the MLC blasts obtained upon cultivating interleukin-2 per se as well as interleukin-2 eluted from an adsorption column containing the novel antibody.

PREPARING THE INTERLEUKIN-2

Figure 1:
FIG. 1 is a showing of the reaction of BJ proteins with the novel antibodies.

Human peripheral blood lymphocytes were purified over Ficoll/Isopaque and incubated for 48 hours at 37° C. in RPMI 2640 medium with 1% PHA in 5% $CO_2$. The cell density was $1 \times 10^6$ cells/ml.

The culture residue was centrifuged and purified by means of fractionated ammonium-sulfate precipitation, gel filtration over Sephadex G 75, and Dyematrix-Blue A chromatography as described with reference to FIGS. 7, 8; and 6 of Biotest Bulletin, supra.

The material was employed to immunize mice.

IMMUNIZING THE MICE

BALB/c mice were immunized i.p. and s.c every 14 days with 100 μg of the preparation emulsified in complete Freund's adjuvant. The mice received a total of 5 injections.

FUSING THE CELLS 4 days after the last injection the mice were sacrificed and the splenocytes fused with the P3-X63-Ag8.653 mouse-myeloma line by the method described in Köhler and Milstein, supra.

In so doing, the splenocytes were mixed with the myeloma cells in a ratio of 11:1, fused by means of PEG 1500 (Roth) and exposed in microtitration plates.

RESULTS 233 of the 333 wells exhibited clone growth.

The residues from these 233 wells were measured in an Elisa test with a microtitration plate coated with human albumin and with one coated with an interleukin-2 preparation.

7 residues exhibited significantly higher extinctions in the Elisa test with the interleukin-2 preparation than with human albumin (e.g. 0.535 with IL-2 as against 0.225 with HA). Among them a clone of the line of hybridoma cells designated BS 50 was produced.

The BS 50 hybridoma-cell line was deposited as Number I-313 with the CNCM on July 5, 1984.

The BS 50 was cloned by the limiting-dilution method. 33 of the 288 depressions exhibited growth of only 1 clone. The residues were again Elisa tested and all 33 depressions exhibited a higher extinction than with human albumin.

RESULTS WITH THE MONOCLONAL ANTIBODY AGAINST PBL HUMAN INTERLEUKIN-2 PRODUCED BY THE BS 50 LINE OF HYBRIDOMA CELLS

1. Inhibition of the Biological Interleukin-2 Test

The biological interleukin-2 was determined with lymphoblasts stimulated with MLC or PHA. The amount of incorporated $^3$H-thymidine was employed as a measure of interleukin-2 activity.

As will be evident from Table 1, the addition of the antibody from BS 50 inhibits the incorporation of $^3$H-thymidine.

Since human interleukin-2 is also active against mouse cells, the inhibition was also measured in that system.

The addition of antibodies from BS 50 also inhibits $^3$H-thymidine incorporation in murine Con A splenoblasts. (This, in addition to the Elisa data, is another proof that the monoclonal antibody addresses itself to IL-2).

TABLE 1

Inhibition of $^3$H—thymidine incorporation by clones produced from BS 50 in IL-2 test

| Test cells | MAB | Dilution of MAB in CPM | | | |
|---|---|---|---|---|---|
| | | 1:40 | 1:100 | 1:200 | 1:400 |
| MLC blasts | BS 50 | 449 | 470 | 894 | 22589 |
| (human) | BS 51 | 544 | 831 | 2644 | 33323 |
| | Control | 133567 | 151459 | 211949 | 210028 |
| | medium | 107332 | 131420 | 181913 | 254612 |
| Con A-stimulated | BS 50 | 303 | 1042 | 6859 | 35508 |
| (mouse splenocytes) | BS 51 | 359 | 603 | 21758 | 28626 |
| | Control | 24462 | 27977 | 33929 | 29539 |

TABLE 1-continued

Inhibition of $^3$H—thymidine incorporation by clones produced from BS 50 in IL-2 test

| Test cells | MAB | Dilution of MAB in CPM | | | |
|---|---|---|---|---|---|
| | | 1:40 | 1:100 | 1:200 | 1:400 |
| | medium | 39952 | 49255 | 27308 | 43140 |

2. Elisa with Various Fractions Subsequent to Gel Filtration of the Residual Interleukin-2

Table 2 shows that the antibody from BS 50 reacts powerfully with the fraction that has a molecular weight of 160 000, significantly with the fraction of molecular weight 45 000, and weakly with the fraction of molecular weight 17 000.

It also shows that the monoclonal antibody recognizes an epitope on the molecular-weight 160 000 and molecular-weight 45 000 protein, which must be present at least twice on these molecules.

In gel filtration interleukin-2 has a molecular weight of 17 000, whereas IgG has one of 160 000. Fab has a molecular weight of 50 000. (This is a preliminary proof that the antibody from BS 50 reacts with IgG, which also explains that the epitope is present twice.)

TABLE 2

Reaction of antibodies produced by BS 50 with three different fractions of an IL-2 preparation by gel chromatography on Sephadex G 75.

| | | Elisa | | |
|---|---|---|---|---|
| Antibody Solid phase | Antibody Liquid phase | Antigen = Residue containing IL-2 purified by gel filtration | | |
| | | MW: 160K | 45K | 17K |
| BS 50 | BS 50 POD | +++ | + | +− |
| BS 50 | Other MAB POD | − | − | − |

3. Elisa with Various Defined Proteins

In order to explain the reaction of the antibody from BS 50 with IgG, Elisa tests were conducted with defined immunoglobulins and portions (IgG, IgG-Fab, and IgG-Gc portions and light λ and κ chains).

As will be evident from Table 3, the antibody from BS 50 reacts significantly in this test with the light λ chain and with immunoglobulins that carry the light λ chain.

TABLE 3

Reaction of the antibodies from BS 50 in the Elisa test with immunoglobulin molecules.

| MAB | Antigen IgA | IgG | IgM monocl. (κ) | BJ λ | BJ κ | FAB | FC |
|---|---|---|---|---|---|---|---|
| BS 50 residue | 0.609 | 0.607 | 0.111 | 0.452 | 0.128 | 0.538 | 0.170 |
| BS 50 ascites 1:4000 | 1.014 | 0.974 | 0.211 | 1/107 | 0.221 | 0.969 | 0.318 |
| BS 51 Residue | 0.140 | 0.172 | 0.121 | 0.124 | 0.189 | 0.243 | 0.215 |
| BS 51 ascites 1:4000 | 0.284 | 0.291 | 0.376 | 0.235 | 0.212 | 0.345 | 0.303 |
| Anti-λ ascites 1:4000 | 0.841 | 0.737 | 0.166 | 0.838 | 0.122 | 0.965 | 0.211 |
| Anti-κ ascites 1:4000 | 0.679 | 0.778 | 0.672 | 0.157 | 0.376 | 0.863 | 0.209 |
| Control | 0.162 | 0.143 | 0.111 | 0.119 | 0.124 | 0.174 | 0.144 |

4. Demonstrating the Existence of the Light λ Chain by SDS Electrophoresis with POD-conjugated Monoclonal Antibodies from BS 50

Bence Jones proteins of the λ and κ types were separated by SDS electrophoresis. The existence of the proteins was demonstrated by a blotting method wherein the protein was transferred from the SDS gel to a nitrocellulose diaphragm and indicated there with the antibody in a direct or indirect test.

Demonstration was carried out directly in this case with POD-conjugated antibody.

As FIG. 1 indicates, the antibody from BS 50 reacts significantly with the light λ chain (MW 25 000).

The weak reaction to κ can be ascribed to contamination with λ.

Bonding Interleukin-2 to Antibodies from BS 50-sepharose Columns

Once the reaction of antibodies from BS 50 to the light λ chain had been successfully demonstrated, light λ chains were removed from interleukin-2 residues by immune adsorption from anti-λ columns for other tests to further investigate this monoclonal antibody with respect to its reaction with interleukin-2.

Figure 2:
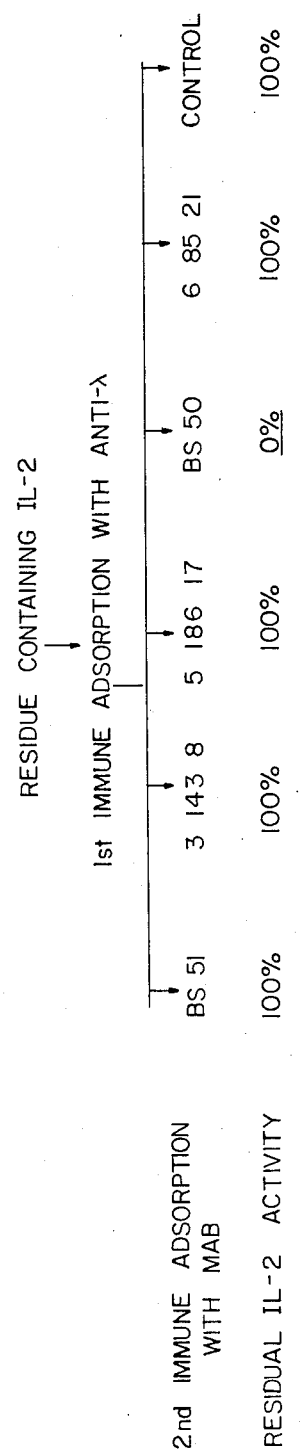
FIG. 2 is a chart showing the interleukin-2 binding activity of several different monoclonal antibodies, including that of the present invention.

The resulting λ-free interleukin-2 residue was then, as illustrated in FIG. 2, supplied in 6 portions to 6 different columns charged with monoclonal antibodies and the interleukin-2 activity determined while they were flowing through.

The monoclonal antibody from BS 50 is the only one of all the antibodies to bond total interleukin-2 activity.

6. Eluting Interleukin-2 from BS 50 Antibody Columns

As the previously described experiment demonstrated, the total activity could be adsorbed.

AS Table 4 shows, 27% of the amount of interleukin-2 introduced was successfully eluted from the BS 50 column.

The monoclonal antibody from BS 50 is accordingly appropriate for the highly specific purification of interleukin-2 assuming that the light λ chain has previously been eliminated.

TABLE 4

Immune adsorption of interleukin-2 on columns of antibodies from BS 50

| Interleukin-2 activity applied | 3840 units = 100% |
|---|---|
| Interleukin-2 activity remaining after immune adsorption with BS 50 | 0 units = 0% |
| Diluted interleukin-2 activity* | 980 units = 27% |

*The interleukin-2 was diluted with 0.5 M propionic acid, 0.1% PEG 6000, and 0.1% HSA.

7. Long-term Growth of Activated T Lymphocytes with Interleukin-2 Eluted from BS 50 Antibodies Whereas the $^3$H-thymidine-incorporation tests are in principle only auxiliary test for determining interleukin-2 activity, even though they are accepted worldwide as an interleukin-2 test, the final demonstration of interleukin-2 activity is the culture of activated T lymphocytes over the long term.

As FIG. 3 shows, human MLC blasts were successfully cultivated for 4 weeks with material eluted from a BS 50 antibody column in comparison with a interleukin-2 preparation.

Thus, the monoclonal antibody produced from the BS 50 hybridoma line exhibits specific reactions with a factor that is essential to the in vitro growth of T lymphocytes and that corresponds in accordance with biochemical criteria to human interleukin-2 and to the light λ chain of human immunoglobulin, meaning that the antibody recognizes the structure that is common to interleukin-2 (TCGF) and to the light λ chain.

It will be understood that the specification and examples are illustrative but not limitative of the present invention and that other embodiments within the spirit and scope of the invention will suggest themselves to those skilled in the art.

We claim:

1. A hybridoma cell line which produces an antibody with specificity to human interleukin-2, and that recognizes a structure common to interleukin-2 (TCGF) and to the light λ chain of human immunoglobulin, the cell line having been obtained by fusing an antibody-producing animal cell with a neoplastic cell.

2. A cell line according to claim 1, wherein the antibody-producing cell is of murine origin.

3. A monoclonal antibody produced from a hybridoma cell line according to claim 2.

4. A cell line according to claim 1, wherein the antibody-producing animal cell is a BALB/c-mouse splenocyte.

5. A monoclonal antibody produced from a hybridoma cell line according to claim 4.

6. A cell line according to claim 1, wherein the neoplastic cell is a myeloma cell.

7. A monoclonal antibody produced from a hybridoma cell line according to claim 6.

8. A cell line according to claim 1, wherein the neoplastic cell is the P3-X63-Ag8.653 myeloma-cell (CNCM I-251) that produces no antibodies.

9. A monoclonal antibody produced from a hybridoma cell line according to claim 1.

10. A method for identifying and detecting interleukin-2 in a patient comprising analyzing the content of interleukin-2 (TCGF) in one of the patients' body fluids by contacting said fluid with a monoclonal antibody according to claim 9.

11. A method for purifying a interleukin-2-containing material comprising removing the light lambda chain and contacting the resultant material with a monoclonal antibody according to claim 9.

12. CNCM I-313 BS 50 hybridoma cell line.

13. A monoclonal antibody produced from a hybridoma cell line according to claim 12.

14. A monoclonal antibody which reacts with an interleukin-2 fraction having a molecular weight of 160,000 reacts with the light lambda chain of human immunoglobulin having a molecular weight of 45,000 and reacts with an interleukin-2 fraction having a molecular weight of 17,000.

* * * * *

UNITED STATES PATENT AND TRADEMARK OFFICE
CERTIFICATE OF CORRECTION

PATENT NO. : 4,751,183

DATED : June 14, 1988

INVENTOR(S) : Hans H. Sonneborn, et al

It is certified that error appears in the above-identified patent and that said Letters Patent is hereby corrected as shown below:

| | |
|---|---|
| Col. 1, line 12 | After "light" insert --$\lambda$-- |
| Col. 2, lines 58-59 | Delete "monoclona" and substitute --monoclonal-- |
| Col. 3, line 68 | After "8" delete ";" and substitute --,-- |
| Col. 6, line 16 | Before "Bonding" insert --5.-- |
| Col. 8, line 9 | Insert space between "-2" and "in" |

Signed and Sealed this

Fourteenth Day of February, 1989

Attest:

DONALD J. QUIGG

*Attesting Officer*  *Commissioner of Patents and Trademarks*